United States Patent
Kuge

(10) Patent No.: US 7,924,006 B2
(45) Date of Patent: Apr. 12, 2011

(54) METHOD AND APPARATUS FOR ANALYZING SAMPLE UTILIZING NUCLEAR MAGNETIC RESONANCE UNDER TERAHERTZ-WAVE IRRADIATION

(75) Inventor: Katsuaki Kuge, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 1026 days.

(21) Appl. No.: 11/738,269

(22) Filed: Apr. 20, 2007

(65) Prior Publication Data

US 2007/0252596 A1 Nov. 1, 2007

(30) Foreign Application Priority Data

May 1, 2006 (JP) ................................. 2006-127829

(51) Int. Cl.
*G01V 3/00* (2006.01)
(52) U.S. Cl. ........................................ 324/309; 324/307
(58) Field of Classification Search .......... 324/300–322; 382/128, 280, 260, 309; 375/350
See application file for complete search history.

(56) References Cited

U.S. PATENT DOCUMENTS

| | | | | |
|---|---|---|---|---|
| 7,202,664 B2 | 4/2007 | Kitagawa | ...................... | 324/307 |
| 7,358,733 B2 * | 4/2008 | Clark et al. | .................... | 324/318 |
| 7,839,145 B2 * | 11/2010 | Cornwell | ...................... | 324/307 |
| 2005/0110495 A1 | 5/2005 | Kitagawa | ...................... | 324/321 |
| 2008/0226137 A1 * | 9/2008 | Benaron et al. | ............... | 382/115 |
| 2009/0075325 A1 * | 3/2009 | Das et al. | .................... | 435/40.52 |
| 2009/0136104 A1 * | 5/2009 | Hajian et al. | .................. | 382/128 |
| 2009/0318815 A1 * | 12/2009 | Barnes et al. | ................. | 600/473 |

FOREIGN PATENT DOCUMENTS

| | | |
|---|---|---|
| JP | 6-317582 | 11/1994 |
| JP | 2002-350377 | 12/2002 |
| JP | 2005-156345 | 6/2005 |

* cited by examiner

*Primary Examiner* — Brij B Shrivastav
(74) *Attorney, Agent, or Firm* — Fitzpatrick, Cella, Harper & Scinto

(57) ABSTRACT

The nuclear magnetic resonance spectrum of a sample, which is a target material analyzed, and changes in relaxation times of nuclear magnetic resonance signals are measured while the sample is irradiated with terahertz waves containing frequency components corresponding to peak portions of absorption or reflectance spectrum of the sample. On the basis of the changes in relaxation times, the relationship between peak portions and information about a three-dimensional structure, conformational alteration, molecular relaxation, and the like is observed, the peak portions being in the absorption or reflectance spectrum in the terahertz range of the sample.

9 Claims, 3 Drawing Sheets

METHOD AND APPARATUS FOR ANALYZING SAMPLE UTILIZING NUCLEAR MAGNETIC RESONANCE UNDER TERAHERTZ-WAVE IRRADIATION

BACKGROUND OF THE INVENTION

1. Field of the Invention

The present invention relates to a method and apparatus for analyzing a sample utilizing nuclear magnetic resonance and terahertz waves to obtain information about a material (sample). In particular, the present invention relates to a method and apparatus for analyzing a sample to obtain information about the three-dimensional structure of the molecule constituting a material, conformational alteration, relaxation, and the like and information about the terahertz-wave absorption or reflectance spectrum (typically, fingerprint spectrum) of the material.

2. Description of the Related Art

Methods of analysis utilizing electromagnetic-wave absorption provide significantly important information for the structural analysis of materials. For example, ultraviolet and visible absorption spectra have been used for characterization of excitation processes of electrons of materials. Near- and mid-infrared absorption spectra utilizing longer wavelengths play a significantly important role in structural and state analyses of organic and inorganic materials by excitation of chemical combination vibration of molecules to form spectra.

In contrast, until recently, terahertz waves (electromagnetic waves having a frequency in the range of several hundreds of gigahertz to several tens of terahertz) lying in the terahertz range, which is a further longer wavelength range, have not been used. However, in recent years, a high-performance light source for generating terahertz waves has been developed. Thus, terahertz waves have recently been receiving attention.

Like radio waves, terahertz waves can penetrate materials and thus provide internal information about materials. Furthermore, fingerprint spectra in the terahertz range provide structural information for identifying materials. That is, terahertz waves can be used for structural analysis that has been performed by the known infrared spectroscopy. The energy of terahertz waves is about two orders of magnitude lower than that of visible light. Thus, terahertz waves are suitably used to observe elementary excitation and relaxation of molecules, i.e., rotary motion of gas molecules, skeletal vibrations of molecules, intermolecular vibrations, and the like.

If peaks in fingerprint spectra lying in the terahertz range could be assigned and analyzed, information about elementary excitation and relaxation of molecules described above can be obtained, which is quite fascinating. In the infrared absorption spectra widely used now, peaks in spectra can be assigned with relatively high accuracy by calculating the combination vibration energy and the like of molecules using abundant spectrum databases, molecular orbital calculation, and the like. This is one reason for the wide use of infrared absorption spectra for molecular structure analysis, state analysis, and the like.

However, currently, peaks of materials in fingerprint spectra lying in the terahertz range are very difficult to assign. In the present circumstances, the number of spectrum data is small, assignments by means of molecular orbital calculation and the like have low accuracy, and the number of examples assigned is also small. This is attributed to the fact that absorption in the terahertz range varies in response to modes of motion of molecules. If peaks in fingerprint spectra lying in the terahertz range could be assigned and analyzed without any inhibition, the fingerprint spectra lying in the terahertz range should be widely used as a material-identifying tool.

From the background and present circumstances, it is desirable to develop an effective method for analyzing a fingerprint spectrum of a material in the terahertz range.

On the other hand, nuclear magnetic resonance (NMR) spectroscopy is a method of analysis of molecular structure and the like of organic materials. For example, when NMR spectra of hydrogen and carbon (to be exact, carbon-13 which is an isotope of carbon) constituting molecules of organic materials are measured, independent signals of all hydrogen and carbon are observed in response to chemical and magnetic environments thereof in the molecules. That is, hydrogen and carbon constituting the organic molecules can be distinguished at the molecular level. Furthermore, it is known that measurement of changes in the relaxation times of nuclear magnetic resonance signals (NMR signals) results in the evaluation of the interaction between materials and the evaluation of molecular mobility.

Japanese Patent Laid-Open No. 2005-156345 discloses a technique for measuring NMR signals of a protein by placing an aqueous solution of a protein sample in a static magnetic field and irradiating the sample with terahertz waves corresponding to a resonance frequency of unpaired spin present at the side chain of the protein sample. In this measurement, the application of a markedly strong magnetic field, for example, 21 T (tesla), to the aqueous solution sample of the protein sample results in Zeeman splitting of the unpaired spin present at the side chain of the protein, the Zeeman split levels being close to the energy of terahertz waves. The unpaired spin is excited by irradiation with terahertz waves corresponding to the resonance frequency of the unpaired spin, resulting in energy transfer via bonds such as hydrogen bonds around the unpaired spin. The change of bonds in the protein in the aqueous solution is observed from a change in the chemical shift of the NMR spectrum.

As described above, a combination of terahertz waves capable of exciting vibration and motion of the entirety of molecules and measurement of relaxation times of NMR signals for evaluation of large molecular mobility results in the assignment of peaks, which have been difficult to assign so far, in terahertz-wave fingerprint spectra. However, the assignment of the peaks in the fingerprint spectra is not reliable. Furthermore, a spectrometric technique for the assignment has not been established.

In the analysis described in Japanese Patent Laid-Open No. 2005-156345, it is essential that a measurement sample has unpaired spin. However, very limited organic materials have such unpaired spin. Thus, the method lacks versatility. Furthermore, in the method described above, the bonding state and the bonding distance in a very limited region around the unpaired spin are controlled and observed. That is, information about dynamic behavior, such as molecular vibration and molecular mobility, is not obtained.

SUMMARY OF THE INVENTION

In consideration of the foregoing problems, a method according to the present invention for analyzing a sample utilizing nuclear magnetic resonance under terahertz-wave irradiation includes a first step to a fourth step described below. In the first step, the sample is irradiated with terahertz waves, and the terahertz-wave absorption spectrum or the terahertz-wave reflectance spectrum of the sample is measured. In the second step, the sample is placed in a static magnetic field, and the nuclear magnetic resonance signal and the relaxation time of the nuclear magnetic resonance signal of the sample are measured. In the third step, the sample is placed in the static magnetic field, and the nuclear magnetic resonance signal and the relaxation time of the nuclear magnetic resonance signal of the sample are measured under terahertz-wave irradiation. In the fourth step, information about the relationship between the spectrum measured in the first step and information about the sample on the basis of the nuclear magnetic resonance signal and the relaxation time of the nuclear magnetic resonance signal measured in each of the second step and the third step are obtained.

Furthermore, in consideration of the problems, an apparatus according to the present invention for analyzing a sample utilizing nuclear magnetic resonance under terahertz-wave irradiation includes a support in which the sample is placed, a terahertz-wave irradiation unit, a terahertz-wave detector, a static-magnetic-field generator, a measurement unit, and an analyzing unit. The terahertz-wave irradiation unit is used to irradiate the sample placed in the support with terahertz waves. The terahertz-wave detector is used to measure the terahertz-wave absorption spectrum or the terahertz-wave reflectance spectrum of the sample placed in the support. The static-magnetic-field generator is used to apply a static magnetic field to the sample placed in the support. The measurement unit is used to measure the nuclear magnetic resonance signal and the relaxation time of the nuclear magnetic resonance signal of the sample placed in the static magnetic field under terahertz-wave irradiation from the terahertz-wave irradiation unit. The analyzing unit is used to obtain information about the relationship between the spectrum measured by the terahertz-wave detector and information about the sample on the basis of the nuclear magnetic resonance signal and the relaxation time of the nuclear magnetic resonance signal measured in the measurement unit in each of the cases where the sample is placed in the static magnetic field and the sample is placed in the static magnetic field under the terahertz-wave irradiation from the terahertz-wave irradiation unit.

Further features of the present invention will become apparent from the following description of exemplary embodiments with reference to the attached drawings.

DESCRIPTION OF THE EMBODIMENTS

Figure 1:
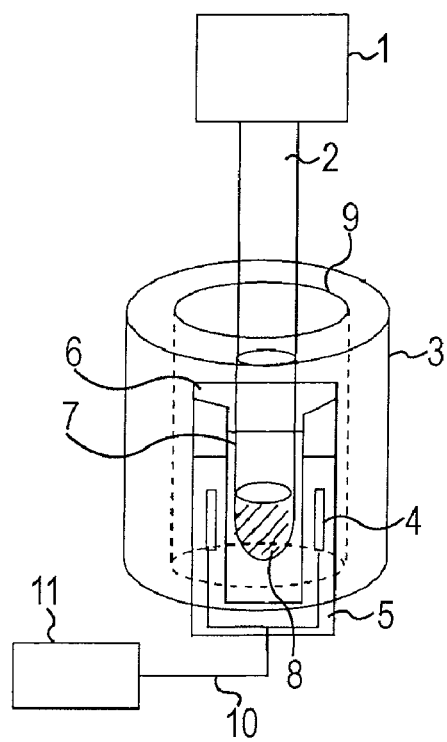
FIG. 1 is a schematic view of the structure of an analyzer that is suitable for performing a method of analysis according to the present invention, the analyzer including a nuclear magnetic resonance unit and a terahertz-wave irradiation unit.

Embodiments and the principle of the present invention will be described below.

To facilitate description, atoms, such as 1H, 13C, 29Si, 15N, and 31P, having a nuclear spin quantum number of ½ will be described. However, the present invention is also applied to the analysis of materials having nuclear spin quantum numbers different from ½. In general, nuclear spin moments of nuclei in a sample are random and are not oriented. Averaging thereof results in no magnetization of the entirety of a material. A sample containing an atom having a nuclear spin quantum number of ½ is placed in a static magnetic field. The energy state of the nuclear spin of the atom in the sample is split into two energy states with an energy split width represented by a predetermined formula, i.e., Zeeman splitting occurs. The lower energy state is a state in which the direction of the nuclear spin moments is parallel to the direction of the static magnetic field. The higher energy state is a state in which the direction of the nuclear spin moments is antiparallel to the direction of the static magnetic field. In each energy state at a specific temperature, the nuclear spin is distributed at a specific rate according to the Boltzmann distribution.

In the case where the sample in this state is irradiated with electromagnetic waves having energy equal to the energy split width, energy absorption occurs. At this point, the frequency of the electromagnetic waves corresponds to a precession rate. This is the resonance frequency of nuclear magnetic resonance (NMR). Electromagnetic-wave pulses containing all frequency components in the resonance frequency range are provided because the energy split width slightly varies (chemical shift) in response to the situation of the nuclei. Then, signals emitted from the sample are free induction decay (FID) signals that are superposed radio waves with a specific decay frequency. The FID signals are subjected to Fourier transform to obtain a spectrum, i.e., a nuclear magnetic resonance spectrum (NMR spectrum), wherein the horizontal axis represents the frequency, which is a shift from the standard resonance frequency of NMR. The shift slightly varies in response to the chemical and magnetic situations of the nuclei. Thus, for example, molecular structure of the material can be determined by the shift.

The FID signals decay over a specific period of time to return to the spin state before the irradiation with the electromagnetic waves having energy corresponding to the energy split width. This phenomenon is referred to as spin relaxation, and a time required for the decay is referred to as a relaxation time. A cause of spin relaxation is molecular motion. The motion of a molecule or an atom in a molecule results in the formation of an oscillating field. The oscillating field impinges on the nuclei excited by the electromagnetic waves to cause deexcitation, resulting in spin relaxation. Thus, it is known that the relaxation time of nuclear magnetic resonance signals (NMR signals) varies in response to the intensity of molecular mobility. Hence, the relaxation time is generally used for the evaluation of the molecular mobility.

In general, for low-molecular-weight organic molecules in a solution, it is known that an increase in the intensity of molecular mobility prolongs relaxation time. Furthermore, from a comparison with an NMR spectrum, the relaxation time of the NMR signal of a specific position in the organic molecule may be measured to evaluate the intensity of the molecular mobility at the specific position.

Irradiating a sample with terahertz waves having a frequency in the range of several hundreds of megahertz to several tens of terahertz excites motion due to rotary motion in a molecule, intermolecular interaction, molecular conformation, conformational alteration, and the like. As a result, absorption occurs and is observed as a spectrum. This shows that irradiating a sample with terahertz waves having a predetermined frequency can induce specific motion of the molecules constituting the sample.

As described above, absorption by a sample is observed by irradiating molecules in the sample measured with terahertz waves having a predetermined frequency. Then, molecular motion corresponding to the absorption is excited to activate the motion. The relaxation time of NMR signals obtained from the sample reflects the activated motion. According to the principle described above, information about a sample corresponding to a fingerprint spectrum can be obtained on the basis of nuclear magnetic resonance signals and the relaxation time of nuclear magnetic resonance signals. Specifically, peaks, which have been difficult to assign so far, in a terahertz-wave fingerprint spectrum can be assigned.

That is, first, a fingerprint spectrum of a sample is measured in the terahertz range. Portions of the frequency of the terahertz waves are determined, the portions corresponding to peaks, to be assigned, observed in the fingerprint spectrum of the sample in the terahertz range. The NMR spectrum of the sample is measured. Peaks in the resulting NMR spectrum are assigned to the corresponding portions in the molecular structure of the sample. Relaxation times of the NMR signals of the sample are measured. Next, an NMR spectrum is measured while the sample is irradiated with terahertz waves containing the portions of the frequency determined in the above step. Relaxation times of the NMR signals in the NMR spectrum are measured. Finally, the resulting relaxation times of the NMR signals are compared with each other before and after the irradiation with the terahertz waves to identify the NMR signals (which have been assigned) in which the relaxation times are changed. For example, the assigned molecular portions of the sample correspond to portions of molecular motion excited by irradiation with the terahertz waves in the above-described step. In this way, the fingerprint spectrum, which has been difficult to assign so far, in the terahertz spectrum can be assigned.

The NMR signals used for measurement of the NMR spectrum and the relaxation time of the sample are not particularly limited, as long as the atomic species can provide NMR signals, i.e., the nucleus has nuclear spin. However, from the standpoint of ease of simplification of a process for obtaining information about the sample, the nucleus desirably has a nuclear spin quantum number of ½. Examples of the type of nucleus include 1H, 13C, 15N, 29Si, 31P, and 19F.

The molecule to be analyzed is not particularly limited, as long as the molecule in which an NMR spectrum and NMR signals can be observed is used. Desirably, the molecule is an organic molecule not having unpaired spin therein, i.e., the molecule is not a paramagnetic organic molecule. It is known that the unpaired spin generally has a large effect on relaxation times of NMR signals from a molecule having the unpaired spin to markedly reduce the relaxation time (paramagnetic relaxation). Thus, in the case where a sample containing a molecule having the unpaired spin is analyzed according to the present invention, it is highly possible that a change in relaxation time due to irradiation with terahertz waves and excitation is very difficult to evaluate. Furthermore, the NMR signals of the NMR spectrum from the target molecule analyzed are broadened to degrade peak resolution. Thus, the molecule having the unpaired spin is not desirable also from the standpoint of peak separation.

The state of the sample used for measurement is desirably a solution. Thus, the target sample is dissolved in a solvent to form a solution. The solvent used for the solution is not particularly limited, as long as the solvent can dissolve the target sample. A deuterated solvent or a mixed solvent containing a predetermined proportion of a deuterated solvent is desirable.

A method for measuring relaxation times of NMR signals is not particularly limited. In general, an inversion recovery method and the Carr-Purcell, Meiboom-Gill (CPMG) method are often used.

A solution, prepared for analysis according to the present invention, of a target sample is desirably used for measurement of the terahertz spectrum of the target sample. Alternatively, the target sample may be measured in a solid state, a liquid state, or a gas state. Desirably, no unnecessary absorption of terahertz waves with which the sample is irradiated occurs in the path to the sample. The wavelength of the terahertz waves with which the target sample is irradiated to obtain a terahertz spectrum can be selected without limitation.

Figure 2:
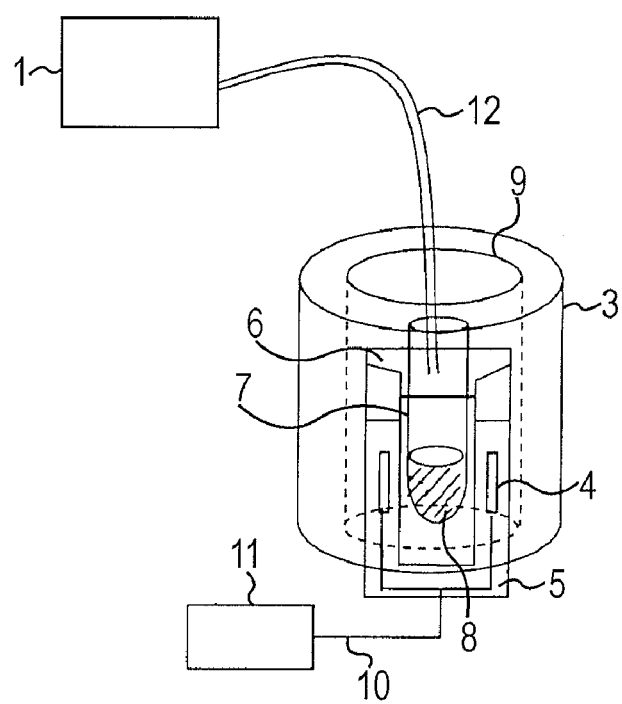
FIG. 2 is a schematic view of another structure of the analyzer shown in FIG. 1.

When the NMR spectrum and the NMR signals are measured, as shown in FIG. 1, a method for directly irradiating the sample with terahertz waves from the upper side may be employed. In the case where the sample is directly irradiated with terahertz waves, the apparatus desirably includes a path filled with a dry nitrogen gas. Most desirably, the inside of an NMR sample tube is directly irradiated with terahertz waves using fibers or the like, as shown in FIG. 2. This structure is used for the prevention of the absorption of water in air and absorption by the sample tube in the step of irradiating the sample with terahertz waves. The structure of the apparatus is not particularly limited, as long as the sample can be efficiently irradiated with terahertz waves.

Embodiments of the apparatuses for analyzing the sample shown in FIGS. 1 and 2 will be described. Each apparatus includes a unit configured to apply a uniform static magnetic field to the sample, an oscillator configured to irradiate the sample with electromagnetic waves in the terahertz range, a probe capable of detecting signals of nuclear magnetic resonance, and an observational unit.

In FIG. 1, the apparatus includes a terahertz oscillator 1, a path 2 for terahertz-wave irradiation, a cylindrical magnet 3 configured to generate a uniform static magnetic field and having a bore 9, and a coil 4 (irradiating and receiving coil) for irradiation with electromagnetic waves for nuclear magnetic resonance and functioning as a nuclear magnetic resonance probe. The apparatus further include a probe main body 5 configured to measure NMR, a holder 6 configured to support a sample tube 7 in which a sample 8 is placed, a circuit line 10 for NMR signal irradiation and the receiving coil, and the main body of a NMR spectrometer 11. A terahertz-electromagnetic-wave detector (not shown) configured to detect terahertz waves from the sample 8 in order to measure a terahertz absorption spectrum or a terahertz reflectance spectrum of the sample 8 is also provided. In FIG. 2, the apparatus includes fibers 12 for irradiation with terahertz waves.

In the apparatuses, the sample is analyzed as follows: the fingerprint spectrum of the sample is measured with the terahertz oscillator 1 and the terahertz-wave detector. Portions of the frequency of the terahertz waves are determined, the portions corresponding to peaks, to be assigned, observed in the fingerprint spectrum of the sample in the terahertz range. After the sample is irradiated with electromagnetic waves for nuclear magnetic resonance using the coil 4 in a magnetic field generated by the magnet 3, the NMR spectrum of the sample is measured with the nuclear magnetic resonance probe. Peaks in the resulting NMR spectrum are assigned to the corresponding portions in the molecular structure and the like of the sample. Relaxation times of the NMR signals in the NMR spectrum of the sample are measured with the coil 4 configured to probe nuclear magnetic resonance. The NMR spectrum measurement, assignment, and relaxation time measurement are performed by the main body of the NMR spectrometer 11.

Next, an NMR spectrum is measured while the sample is irradiated with terahertz waves containing the portions of the frequency using the terahertz oscillator 1. Relaxation times of the NMR signals in the NMR spectrum are measured. Finally, the resulting relaxation times of the NMR signals are compared with each other before and after the irradiation with the terahertz waves to identify the NMR signals (which have been assigned) in which the relaxation times are changed. The NMR spectrum measurement, relaxation time measurement, relaxation time comparison, and the like are performed by the main body of the NMR spectrometer 11.

For example, the assigned molecular portions of the sample correspond to portions of molecular motion excited by irradiation with the terahertz waves in the above-described step. In this way, the fingerprint spectrum, which has been difficult to assign so far, in the terahertz spectrum can be assigned. That is, information about the relationship between information (molecular structure and the like) about the material and target portions in the terahertz spectrum (typically, the fingerprint spectrum) can be obtained.

In the above-described structure, the sample tube 7 and the holder 6 constitute a support configured such that the sample 8 can be placed in the support. The terahertz oscillator 1 and the path 2 for terahertz-wave irradiation or the fibers 12 for terahertz-wave irradiation constitute a terahertz-wave irradiation unit configured to irradiate the sample 8 placed in the support with terahertz waves. The cylindrical magnet 3 having the bore 9 constitutes a static-magnetic-field generator configured to apply a static magnetic field to the sample 8 placed in the support. The coil 4, the probe main body 5, and the main body of the NMR spectrometer 11 constitute a measurement unit configured to measure the nuclear magnetic resonance signal and the relaxation time of the nuclear magnetic resonance signal of the sample placed in the static magnetic field under terahertz-wave irradiation from the terahertz-wave irradiation unit. The main body of the NMR spectrometer 11 constitutes an analyzing unit configured to obtain information about the relationship between the target portions of the spectrum measured by the terahertz-wave detector and information about the sample on the basis of the nuclear magnetic resonance signal and the relaxation time of the nuclear magnetic resonance signal measured in the measurement unit. The terahertz waves may have a single frequency. Furthermore, the sample may be irradiated with terahertz waves that are in the form of pulses or continuous waves.

EXAMPLES

EXAMPLES of the present invention will now be described.

Example 1

EXAMPLE 1 is an example of a method for analyzing alanine utilizing proton NMR signals under terahertz-wave irradiation of the present invention.

Figure 3:
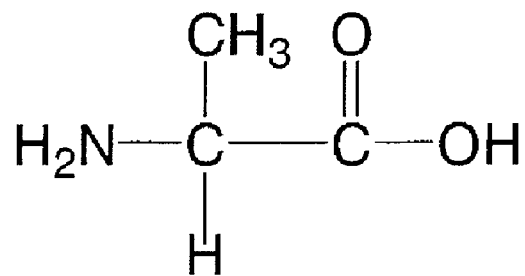
FIG. 3 shows a molecular structure of alanine.
Figure 4:
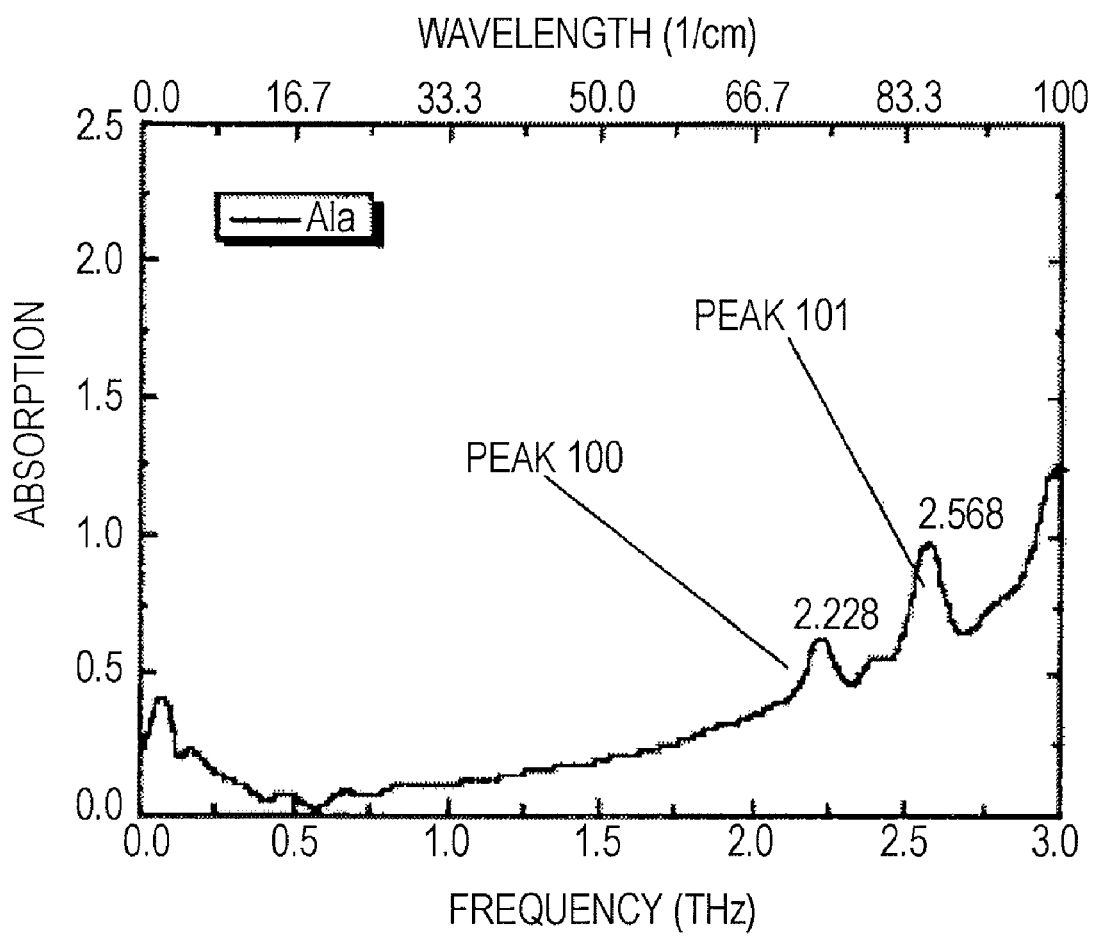
FIG. 4 is a graph showing an absorption spectrum of alanine in the terahertz range.

In this EXAMPLE, first, the terahertz-wave spectrum of alanine is measured. Alanine has a molecular structure shown in FIG. 3. It is known that alanine has an absorption spectrum in the terahertz range. The spectrum of alanine as shown in FIG. 4 is measured (for example, see "Japan's Exposition of Analytical Instruments and Solutions 2005: Teraherutsu, ensekigai bunkouhou nyumon (Introduction to Terahertz and Far-Infrared Spectroscopy), NTT Basic Research Laboratories, Katsuhiro Ajito"). In FIG. 4, elementary excitation and relaxation, such as conformational alteration and rotary motion, in a specific molecule of alanine occur at a frequency of about 2.2 THz (peak 100 in FIG. 4) or about 2.6 THz (peak 101 in FIG. 4), which is a frequency at which the peak is observed.

Figure 5A:
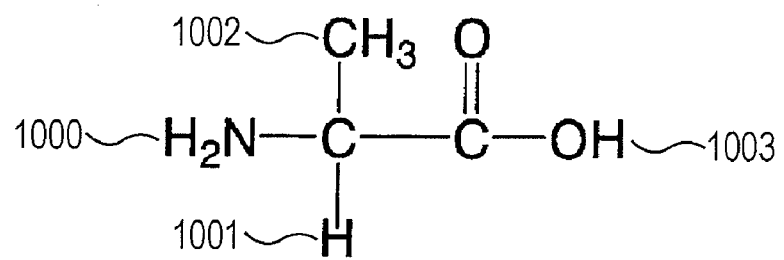
FIGS. 5A and 5B illustrate the assignment of peaks in a proton NMR spectrum to protons in the alanine molecule.

Next, alanine is dissolved in a deuterated solvent. The proton NMR spectrum of alanine is normally measured to obtain the NMR spectrum shown in FIG. 5B. Peaks shown in the FIG. 5B can be easily assigned to hydrogen atoms in the alanine molecule shown in FIG. 5A (peaks 1000, 1001, 1002, and 1003). The NMR signals from the specific hydrogen atoms in the alanine molecule are observed by assigning the peaks in the proton NMR spectrum.

Relaxation times of the proton NMR signals of alanine are measured by an inversion recovery method without terahertz-wave irradiation with respect to the NMR signals from the hydrogen atoms. From this measurement, the relaxation times of the NMR signals due to all of the hydrogen atoms in the alanine molecule can be measured.

Figure 5B:
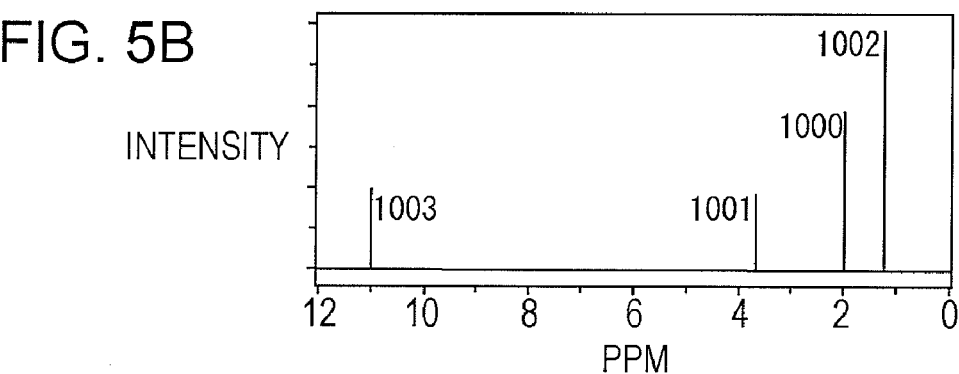

The peak in which a mode of motion will be assigned is chosen from the peaks observed in the terahertz spectrum shown in FIG. 4. The frequency (peak 100: about 2.2 THz or peak 101: about 2.6 THz) of the resulting peak is appropriately chosen. For example, when the peak 100 in FIG. 4 is assigned, the relaxation times of the proton NMR signals observed as in FIG. 5B are measured while alanine is irradiated with terahertz waves having a frequency of about 2.2 THz. From this measurement, the relaxation times of the NMR signals due to all of the hydrogen atoms in the alanine molecule under terahertz-wave irradiation can be measured.

Finally, the NMR signal in which the relaxation time is changed before and after the terahertz-wave irradiation is identified. It is assumed that aniline is irradiated with terahertz waves having a frequency of about 2.2 THz corresponding to the peak 100 in FIG. 4 and that the relaxation time of the peak 1002 in the proton NMR signals shown in FIG. 5B is changed. In this case, the results demonstrate that the mode of motion assigned to the peak 100 in the terahertz spectrum in FIG. 4 relates to the conformational alteration around the protons 1002 in FIG. 5A. The same operation is performed for the peak 101 in the terahertz spectrum shown in FIG. 4. Thereby, it is possible to easily know which portion of the alanine molecule is subjected to elementary excitation and relaxation to form the peak 101 in the terahertz spectrum shown in FIG. 4. Thereby, the modes of the elementary excitation and relaxation of the alanine molecule can be assigned to the peaks in the fingerprint spectrum in the terahertz range.

These steps are performed with the apparatus shown in FIG. 1 or 2. The results are analyzed by the analyzing unit to analyze the material.

Example 2

EXAMPLE 2 is an example of a method for analyzing alanine utilizing carbon NMR signals under terahertz-wave irradiation of the present invention.

First, the terahertz-wave spectrum of alanine is measured to obtain the spectrum as in EXAMPLE 1. The frequency of terahertz waves used for irradiation in this EXAMPLE is equal to 2.2 THz (peak 100 in FIG. 4) or 2.6 THz (peak 101 in FIG. 4), which is a frequency at which the peak is observed in FIG. 4.

Figure 6A:
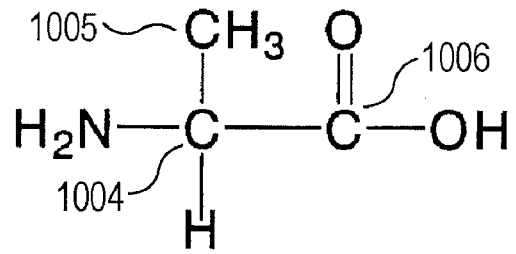
FIGS. 6A and 6B illustrate the assignment of peaks in a carbon NMR spectrum to carbon atoms in the alanine molecule.

Next, alanine is dissolved in a deuterated solvent. The carbon NMR spectrum of alanine is normally measured to obtain the NMR spectrum shown in FIG. 6B. Peaks shown in the FIG. 6B can be easily assigned to carbon atoms in the alanine molecule shown in FIG. 6A (peaks 1004, 1005, and 1006). The NMR signals from the specific carbon atoms in the alanine molecule are observed by assigning the peaks in the carbon NMR spectrum.

Relaxation times of the carbon NMR signals of alanine are measured by an inversion recovery method without terahertz-wave irradiation with respect to the NMR signals from the carbon atoms. From this measurement, the relaxation times of the NMR signals due to all of the carbon atoms in the alanine molecule can be measured.

Figure 6B:
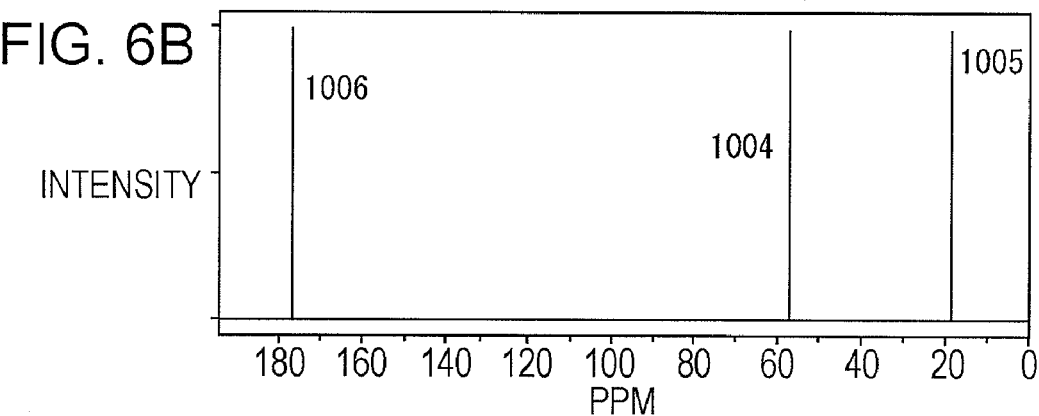

The peak in which a mode of motion will be assigned is chosen from the peaks observed in the terahertz spectrum shown in FIG. 4. The frequency (peak 100: about 2.2 THz or peak 101: about 2.6 THz) of the resulting peak is appropriately chosen. When the peak 100 in FIG. 4 is assigned, the relaxation times of the carbon NMR signals observed as in FIG. 6B are measured while alanine is irradiated with terahertz waves having a frequency of about 2.2 THz. From this measurement, the relaxation times of the NMR signals due to all of the carbon atoms in the alanine molecule under terahertz-wave irradiation can be measured.

Finally, the NMR signal in which the relaxation time is changed before and after the terahertz-wave irradiation is identified. It is assumed that aniline is irradiated with terahertz waves having a frequency of about 2.2 THz corresponding to the peak 100 in FIG. 4 and that the relaxation time of the peak 1005 in the carbon NMR signals shown in FIG. 6B is changed. In this case, the results demonstrate that the mode of motion assigned to the peak 100 in FIG. 4 relates to the conformational alteration around the carbon 1005 in FIG. 6A. The same operation is performed for the peak 101 in the terahertz spectrum shown in FIG. 4. Thereby, it is possible to easily know which portion of the alanine molecule is subjected to elementary excitation and relaxation to form the peak 101 in the terahertz spectrum shown in FIG. 4. Thereby, the modes of the elementary excitation and relaxation of the alanine molecule can be assigned to the peaks in the fingerprint spectrum in the terahertz range.

These steps are also performed with the apparatus shown in FIG. 1 or 2. The results are analyzed by the analyzing unit to analyze the material.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions.

This application claims the benefit of Japanese Application No. 2006-127829 filed May 1, 2006, which is hereby incorporated by reference herein in its entirety.

What is claimed is:

1. A method for analyzing a sample utilizing nuclear magnetic resonance under terahertz-wave irradiation, comprising:
   a first step of irradiating the sample with terahertz waves and measuring the terahertz-wave absorption spectrum or the terahertz-wave reflectance spectrum of the sample;
   a second step of placing the sample in a static magnetic field and measuring the nuclear magnetic resonance signal and the relaxation time of the nuclear magnetic resonance signal of the sample;
   a third step of placing the sample in the static magnetic field and measuring the nuclear magnetic resonance signal and the relaxation time of the nuclear magnetic resonance signal of the sample under terahertz-wave irradiation; and
   a fourth step of obtaining information about the relationship between the spectrum measured in the first step and information about the sample on the basis of the nuclear magnetic resonance signal and the relaxation time of the nuclear magnetic resonance signal measured in each of the second step and the third step.

2. The method for analyzing a sample according to claim 1, wherein the third step includes a substep of measuring the nuclear magnetic resonance signal and the relaxation time of the nuclear magnetic resonance signal of the sample while the sample is irradiated with terahertz waves including waves of a frequency absorbed by the sample.

3. The method for analyzing a sample according to claim 1, wherein the terahertz waves have a single frequency.

4. The method for analyzing a sample according to claim 1, wherein the sample is an organic material.

5. The method for analyzing a sample according to claim 1, wherein the sample is a solution.

6. The method for analyzing a sample according to claim 1, wherein in the second and third steps, the nuclear magnetic resonance signal is due to a hydrogen, carbon, nitrogen, silicon, fluorine, or phosphorus atom.

7. The method for analyzing a sample according to claim 1, wherein in the first step, the terahertz waves are irradiated through a path filled with a dry nitrogen gas.

8. The method for analyzing a sample according to claim 1, wherein in the first step, the terahertz waves are irradiated through a fibrous material.

9. An apparatus for analyzing a sample utilizing nuclear magnetic resonance under terahertz-wave irradiation, comprising:
   a support configured such that the sample is placed in the support;
   a terahertz-wave irradiation unit configured to irradiate the sample placed in the support with terahertz waves;
   a terahertz-wave detector configured to measure the terahertz-wave absorption spectrum or the terahertz-wave reflectance spectrum of the sample placed in the support;
   a static-magnetic-field generator configured to apply a static magnetic field to the sample placed in the support;
   a measurement unit configured to measure the nuclear magnetic resonance signal and the relaxation time of the nuclear magnetic resonance signal of the sample placed in the static magnetic field under terahertz-wave irradiation from the terahertz-wave irradiation unit; and
   an analyzing unit configured to obtain information about the relationship between the spectrum measured by the terahertz-wave detector and information about the sample on the basis of the nuclear magnetic resonance signal and the relaxation time of the nuclear magnetic resonance signal measured in the measurement unit in each of the cases where the sample is placed in the static magnetic field and the sample is placed in the static magnetic field under the terahertz-wave irradiation from the terahertz-wave irradiation unit.

\* \* \* \* \*